(12) United States Patent
Chazallet

(10) Patent No.: US 10,571,667 B2
(45) Date of Patent: Feb. 25, 2020

(54) DEVICE AND METHOD FOR IMAGING AN OBJECT BY ARRANGING A REFLECTIVE OPTICAL SURFACE OR REFLECTIVE OPTICAL SYSTEM AROUND THE OBJECT

(71) Applicants: ARVALIS INSTITUT DU VEGETAL, Paris (FR); BIOGEMMA, Paris (FR); SHAKTI, Marseilles (FR)

(72) Inventor: Frederic Chazallet, Marseilles (FR)

(73) Assignees: ARVALIS INSTITUT DU VEGETAL, Paris (FR); BIOGEMMA, Paris (FR); SHAKTI, Marseilles (FR)

( * ) Notice: Subject to any disclaimer, the term of this patent is extended or adjusted under 35 U.S.C. 154(b) by 670 days.

(21) Appl. No.: 15/103,204

(22) PCT Filed: Dec. 10, 2014

(86) PCT No.: PCT/FR2014/053250
§ 371 (c)(1),
(2) Date: Jun. 9, 2016

(87) PCT Pub. No.: WO2015/086988
PCT Pub. Date: Jun. 18, 2015

(65) Prior Publication Data
US 2018/0143410 A1  May 24, 2018

(30) Foreign Application Priority Data

Dec. 10, 2013 (FR) .................................... 13 02875
Dec. 9, 2014 (FR) .................................... 14 62125

(51) Int. Cl.
*G02B 13/06* (2006.01)
*G03B 17/17* (2006.01)
(Continued)

(52) U.S. Cl.
CPC ............. *G02B 13/06* (2013.01); *G01N 21/85* (2013.01); *G01N 21/952* (2013.01); *G03B 15/00* (2013.01);
(Continued)

(58) Field of Classification Search
CPC ...... G02B 13/06; G02B 17/002; G02B 21/04; G02B 21/36–362; G02B 21/367;
(Continued)

(56) References Cited

U.S. PATENT DOCUMENTS 5,126,872 A * 6/1992 Birkle .................. G01N 21/952
356/24
6,128,143 A 10/2000 Nalwa
(Continued)

FOREIGN PATENT DOCUMENTS

WO WO 2006/087176 A1 8/2006
WO WO 2009/067622 A1 5/2009

OTHER PUBLICATIONS

Genovese, K. et al. "360-deg Measurement on Tubular Samples with Axial Stereogrammetry", SEM Annual Conference and Exposition on Experimental and Applied Mechanics 2006, Society for Experimental Mechanics, Jan. 2006, pp. 1-11.
(Continued)

*Primary Examiner* — Ryan S Dunning
(74) *Attorney, Agent, or Firm* — Oblon, McClelland, Maier & Neustadt, L.L.P.

(57) ABSTRACT

A device for taking images of an article, the device including: a reflective optical system extending around an axis of symmetry, including a recess centered on the axis of symmetry and including at least one reflecting surface facing towards the axis of symmetry; and at least one imager arranged to capture at least one image of at least a portion of the article as reflected by the reflecting surface(s) sub-
(Continued)

stantially parallel to the axis of symmetry when the reflective optical system is arranged around the portion of the article.

25 Claims, 7 Drawing Sheets

(51) Int. Cl.

| | | |
|---|---|---|
| *G03B 37/02* | (2006.01) | |
| *G01N 21/952* | (2006.01) | |
| *G01N 21/88* | (2006.01) | |
| *G01N 33/02* | (2006.01) | |
| *F21K 5/06* | (2006.01) | |
| *G03B 15/00* | (2006.01) | |
| *G03B 37/00* | (2006.01) | |
| *G01N 21/85* | (2006.01) | |
| *G01N 21/84* | (2006.01) | |
| *G03B 37/04* | (2006.01) | |
| *G06T 1/00* | (2006.01) | |

(52) U.S. Cl.
CPC ......... *G03B 15/0442* (2013.01); *G03B 17/17* (2013.01); *G03B 37/00* (2013.01); *G03B 37/02* (2013.01); *G01N 33/025* (2013.01); *G01N 2021/8466* (2013.01); *G03B 37/04* (2013.01); *G06T 1/0007* (2013.01); *G06T 2207/30188* (2013.01)

(58) Field of Classification Search
CPC .... G02B 26/12; G03B 15/00; G03B 15/0442; G03B 17/17; G03B 37/00; G03B 37/02; G03B 37/04; G01N 2021/8841; G01N 2021/8466; G01N 21/85; G01N 21/952; G01N 33/025; G06K 9/00657; G06T 1/0007; G06T 2207/30188
USPC ...... 348/42, 45–50, 89, 92, 125; 353/98, 99; 356/12, 237.2, 611; 359/325, 333, 335, 359/336, 376, 462, 535, 618, 639, 640, 359/850–869; 385/133; 396/19–21, 155, 396/324
See application file for complete search history.

(56) References Cited

U.S. PATENT DOCUMENTS

| | | | |
|---|---|---|---|
| 6,333,826 B1 | 12/2001 | Charles | |
| 6,449,103 B1 | 9/2002 | Charles | |
| 2002/0146248 A1 | 10/2002 | Herman et al. | |
| 2004/0247161 A1 | 12/2004 | Storm | |
| 2006/0002605 A1* | 1/2006 | Chang | G01N 21/952 382/141 |
| 2008/0013820 A1* | 1/2008 | Vertoprakhov | G01N 21/8806 382/141 |
| 2008/0265141 A1 | 10/2008 | Leuenberger et al. | |
| 2009/0079838 A1 | 3/2009 | Storm | |
| 2009/0152285 A1* | 6/2009 | Kearney | B60N 3/106 220/737 |
| 2009/0161102 A1 | 6/2009 | Deppermann et al. | |
| 2011/0310244 A1* | 12/2011 | Schweitzer | G01N 21/896 348/92 |
| 2012/0061586 A1* | 3/2012 | Yao | G01N 21/6456 250/459.1 |
| 2012/0257021 A1* | 10/2012 | Kira | H04N 13/243 348/47 |
| 2014/0023243 A1* | 1/2014 | Nagaraj | G06K 9/00624 382/110 |
| 2014/0092267 A1 | 4/2014 | Storm | |
| 2015/0009320 A1* | 1/2015 | Klein | G01N 21/958 348/128 |

OTHER PUBLICATIONS

International Search Report dated Mar. 6, 2015 in PCT/FR2014/053250.

Jiancheng Jia, "Seed maize quality inspection with machine vision" SPIE, Computer Vision for Industry, vol. 1989, XP002507235, Jun. 24, 1993, pp. 288-295.

* cited by examiner

DEVICE AND METHOD FOR IMAGING AN OBJECT BY ARRANGING A REFLECTIVE OPTICAL SURFACE OR REFLECTIVE OPTICAL SYSTEM AROUND THE OBJECT

TECHNICAL FIELD

The present invention relates to a device for taking images of an article, in particular a device for taking peripheral images of an article of elongate shape, and it also relates to a method of taking images of an article by using such a device.

STATE OF THE ART

It is known to determine a property of an article by processing images of the article.

Patent application US 2009/046890 describes a method and a system for analyzing digital images of an ear of maize, for the purpose of determining at least one property of the ear and the maize kernels, in particular the number and size of the kernels.

The system includes an image sensor such as a charge coupled device (CCD) camera, which delivers images to image processor means that apply various processing algorithms to the images, such as filtering or searching for outlines, for example.

Nevertheless, taking images of ears arranged on a support such as a conveyor does not enable a complete view of the ear to be obtained and only enables an approximate estimate of the properties of the ear and its kernels to be obtained.

Such methods and systems for taking images of an article are not suitable for in situ determination of properties of an article in a confined environment, on the basis of images of the article, and in particular for the determination of a property of a portion of a plant such as an ear of maize on a plant that is growing.

Specifically, an article placed in a confined environment often cannot have images taken of its entire peripheral surface because of the minimum spacing distance between the article and the image-taking device that needs to be ensured in order to obtain images of the article, and/or because of obstacles surrounding the article and preventing the image-taking device being moved around the article.

SUMMARY OF THE INVENTION

An object of the invention is to propose a method and a device for taking images of an article, and in particular a method and a device for taking images of the periphery of an article of elongate shape, which method and device are improved and/or remedy, at least in part, the shortcomings or drawbacks of known methods and devices for taking images of an article.

In an aspect of the invention, there is proposed a method of taking images of an article, the method comprising the following steps:
surrounding at least a portion of the article that extends along a longitudinal axis with at least one reflecting surface facing towards the longitudinal axis, i.e. for which a vector normal to the reflecting surface is directed towards the longitudinal axis; and
capturing at least one image of at least a (peripheral) portion of the article, which image is reflected by the reflecting surface(s) substantially parallel to the longitudinal axis.

In another aspect of the invention, there is provided a device for acquiring images of an article, the device comprising:
a hollowed-out reflective optical system extending around an axis (referred to herein by the term "axis of symmetry") and including at least one reflecting surface directed towards the axis; and
at least one image sensor arranged to capture at least one image of at least a (peripheral) portion of the article, which image is reflected by the reflecting surface(s) substantially parallel to the axis of the reflective optical system when the reflective optical system is arranged around the (peripheral) portion of the article.

In another aspect of the invention, there is provided a device for taking images of an article, the device comprising:
a reflective optical system extending around an axis of symmetry, having a recess centered on the axis of symmetry and including at least one reflecting surface facing towards the axis of symmetry; and
at least one imager arranged to capture at least one image of at least a portion of the article as reflected by the reflecting surface(s) substantially parallel to the axis of symmetry when the reflective optical system is arranged around the portion of the article.

The "radial" reflection of images observing all or part of the peripheral surface of the article parallel to the axis of the reflective optical system and/or the longitudinal axis of the article by means of the hollowed-out reflective optical system through which the article can extend and move makes it easier to take "panoramic" images of the entire periphery of at least a longitudinal portion—or slice—of the article, in situ, in particular when the article is surrounded by nearby obstacles.

When the respective dimensions of the reflective optical system and of the article, in particular the length of the article, do not enable a complete peripheral image of the article to be obtained in a single take, image taking may be repeated as often as necessary in order to "scan" the entire periphery of the article by moving the article through the recess in the reflective optical system between two successive image takes—with movement being relative between the device and the article, which may itself remain stationary—and then by "splicing" pairs of images taken in succession.

The movement of the device relative to the article is preferably achieved while keeping the article substantially centered in the recess, and/or while keeping the axis of the reflective optical system substantially in coincidence with the longitudinal axis of the article—or at least of the portion of the article being imaged.

For this purpose, the device may include means for centering the article in the recess, in particular members for bearing against the article, which members are mounted to be movable relative to the reflective optical system along "radial" axes extending in a plane perpendicular to the axis of the reflective optical system.

In order to obtain a device that is particularly compact, with the reflective optical system lying (extending) inside a first cylinder and the recess lying (extending) inside a second cylinder coaxial with the first cylinder—and of smaller radius—, it is possible to dimension the reflective optical system in such a manner that the radius of the first cylinder is less than or equal to three times or twice the radius of the second cylinder.

For example, the radius of the second cylinder may be about 2 to 5 centimeters and the radius of the first cylinder may be equal to the radius of the second cylinder plus about 1 to 3 centimeters.

Preferably, the device includes a transparent window of cylindrical shape, in particular of circular section, around which the reflective optical system extends, thereby making it possible in particular to avoid contact between the article and the reflective optical system, and also to avoid image zones being masked by a portion of the article that masks (interrupts) the beam that is reflected by the reflective optical system.

The reflective optical system may comprise a single reflecting surface that is warped, i.e. non-plane, and that presents symmetry of revolution about an axis of revolution (which then constitutes said axis of symmetry).

Under such circumstances, the reflecting surface is preferably arranged in such a manner that the axis of revolution of the reflecting surface is close to (and parallel to)—and in particular substantially coincides with—the longitudinal axis of the portion of the article that is surrounded by the reflecting surface.

Alternatively, the reflective optical system may comprise a plurality of reflecting surfaces that may be warped (in particular slightly convex) or plane, and that are preferably regularly spaced apart/arranged around an axis (referred to herein by the term "axis of symmetry") that may coincide with the longitudinal axis of the portion of the article that is surrounded by the reflecting surfaces.

Under such circumstances, the number of reflecting surfaces is generally equal to at least three and in particular is equal to at least four, e.g. being equal to eight.

Particularly when the reflecting surfaces are plane, they may be identical in shape and dimensions, in particular they may be substantially trapezoidal in shape.

The plane reflecting surfaces are preferably inclined relative to the axis of symmetry of the reflecting surfaces and/or relative to the longitudinal axis of the portion of the article that is surrounded by the reflecting surface(s), at an acute angle of inclination that is common to the reflecting surfaces. In the same manner, the warped reflecting surface(s) is/are preferably inclined relative to the axis of symmetry or of revolution, with an acute angle of inclination so that the reflecting surface(s) is/are directed towards the axis of symmetry or of revolution, and towards the longitudinal axis of the portion of the article that is surrounded by the reflecting surface(s).

This angle of inclination may be substantially equal to 45 degrees. When the angle of inclination is less than 45 degrees, that leads to the image of the article being magnified by less than one, which may enable the system to be more compact, possibly to the detriment of its resolution.

The warped reflecting surface(s) preferably extend(s) along a frustoconical surface.

The reflecting surface(s) may be partially reflecting and partially transmissive or transparent, in order to pass a light beam for illuminating the surface of the article through the reflecting surface(s).

In order to capture peripheral images of the article as reflected by the reflecting surface(s), it is possible to arrange a single imager having a lens of diameter that is preferably substantially equal to the largest outside dimension of the reflective optical system constituted by the reflecting surface(s), and having an optical axis that is close to (and substantially parallel to)—in particular substantially coincides with—the longitudinal axis of the portion of the article that is surrounded by the reflective optical system, and substantially coincides with the axis of symmetry or of revolution.

In order to use a single imager of smaller dimensions, it is possible to arrange a beam-folding device on the light path between the imager and the reflecting surface(s).

The beam-folding device may include a second hollowed-out reflective optical system extending around an axis coinciding with the axis of the first hollowed-out reflective optical system, and a third reflective optical system on the same axis as the first and second reflective optical systems, so that the three reflective optical systems reflect peripheral images of the article substantially parallel to the axis of the first reflective optical system, and at a smaller distance away from said axis.

With a single imager, the image that is obtained of the periphery of a longitudinal portion—or slice—of the article lies within a ring, in particular when the reflecting surface is frustoconical and a portion of the article extends along the axis of symmetry of the reflective optical system.

The image that is obtained may be separated into two images for a warped optical system (that is not piece-wise plane) when no portion of the article intersects (lies on) the axis of symmetry of the reflective optical system.

It is then preferable to use an optical system that is piece-wise plane (or slightly convex) so as to assemble segmented images on the single imager that are obtained by one or more reflections on planes, and thus with no or very little aberration and/or distortion.

Such an image may be subjected to mathematical processing transforming it into an image in the form of a strip corresponding to a peripheral view of the slice "rolled out flat", and to other processing for determining properties of the article.

Alternatively, a plurality of imagers may be provided with respective optical axes that are spaced apart from (and parallel to) the axis of symmetry or of revolution of the first reflective optical system.

Under such circumstances, each of the images obtained corresponds to only a portion of the periphery of the article, and may be in the form of a ring sector; these images may overlap partially in pairs and may then be subjected to processing enabling the images to be "spliced" together in pairs so as to obtain an image of the entire periphery of at least one "slice" of the article.

These sector-shaped images may be transformed into rectangular images by eliminating from the images image portions that are close to the "joins" between two adjacent reflecting faces, which are projected on two adjacent reflecting faces.

In an embodiment, it is possible to place the respective optical axes of the imagers in regular manner around the axis of symmetry or of revolution of the first reflective optical system.

Under such circumstances in particular, the imagers may be mounted on at least one ring-shaped support presenting a (second) recess centered on the axis of symmetry/revolution of the first reflective optical system.

Such a hollowed-out imager support can co-operate with the first hollowed-out reflective optical system, and where appropriate with the transparent window of cylindrical or tubular shape, to contribute to defining a cavity that is suitable for receiving (the entire) article that is to be observed/imaged, in particular a cavity of elongate cylindrical shape along the axis of symmetry or of revolution of the first respective optical system and of diameter that is greater than the diameter of the smallest cylinder in which the article can be inscribed.

Each imager may comprise a matrix image sensor, in particular a sensor making use of CDD technology or of complementary metal-oxide semiconductor (CMOS) technology, which may include one or several millions of pixels.

The device may include at least one light source arranged to illuminate a portion for imaging of a periphery of the article, in particular by using the first reflective optical system to reflect a light beam emitted by the light source along a lighting axis that is inclined little, if at all, relative to the axis of the first reflective optical system.

The device may also include at least one aiming light source arranged to form a light mark on a portion for imaging of the periphery of the article, in particular by using the first reflective optical system to reflect a second light beam emitted by the aiming source along an aiming axis that slopes little, if at all, relative to the axis of the first reflective optical system.

In particular, the second light beam for aiming may be a flat beam suitable for forming a light mark in the form of a line segment.

This beam reflected by the first reflective optical system may extend in a plane having its normal slightly inclined relative to the optical axis at a determined angle of inclination in order to make triangulation operations possible. Another configuration may be selected in order to avoid potential overlap of the beams; it consists in generating a beam in a plane that substantially includes the optical axis and that enables measurements to be made of distance along the axis of the article and thus of its inclination.

The trace of the aiming light mark in the image that is obtained of the article can be used to determine the distances respectively between the first reflective optical system (and/or the transparent window) and points on the peripheral surface of the article.

The association of this distance information with points of an image that is obtained can thus make it possible to obtain a three-dimensional "pseudo" image (i.e. a model) of the peripheral surface of the article.

The device may also process the overlaps of two images reflected by a determined reflecting surface of the reflective optical system, and captured respectively by two sensors that are neighboring and/or adjacent, thus making it possible to construct a 3D model of the peripheral surface of the article by the stereoscopic effect.

If it is possible to combine distance information between the measurements obtained by the aiming source and the stereoscopic measurements, then it is also possible to use aiming sources that generate one or more points of light that are distributed randomly so as to create on the article a unique light pattern that is easily detectable by two neighboring sensors, thereby simplifying stereoscopic measurements.

The device may include at least one signal and/or data processor unit that is connected to the image sensor(s) and arranged (in particular programmed) to perform at least some of the image processing required for determining a property of the article from images acquired by the sensor(s) or imager(s).

The device may also include a data storage unit connected to the data processor unit and arranged to store image data delivered by the processor unit.

The device may also include a battery—or some other source of electrical energy—arranged to power the image sensor(s), the lighting or aiming source(s), the data processor unit, and the data storage unit.

The invention may be applied in particular to taking images of portions of growing plants without any need to separate a portion for imaging from the remainder of the plant.

The invention makes it possible to obtain an imaging device that is compact and lightweight, that can be cordless, and that can easily be carried and moved by a human being, by a vehicle, or by a carrier robot or vehicle, or by any other device, in order to be engaged around the article for imaging.

Other aspects, characteristics, and advantages of the invention appear from the following description that refers to the accompanying figures and that illustrates preferred embodiments of the invention without any limiting character.

DETAILED DESCRIPTION OF THE INVENTION

Unless specified explicitly or implicitly to the contrary, elements or members that are structurally or functionally identical or similar are given identical references in the various figures.

Figure 1:
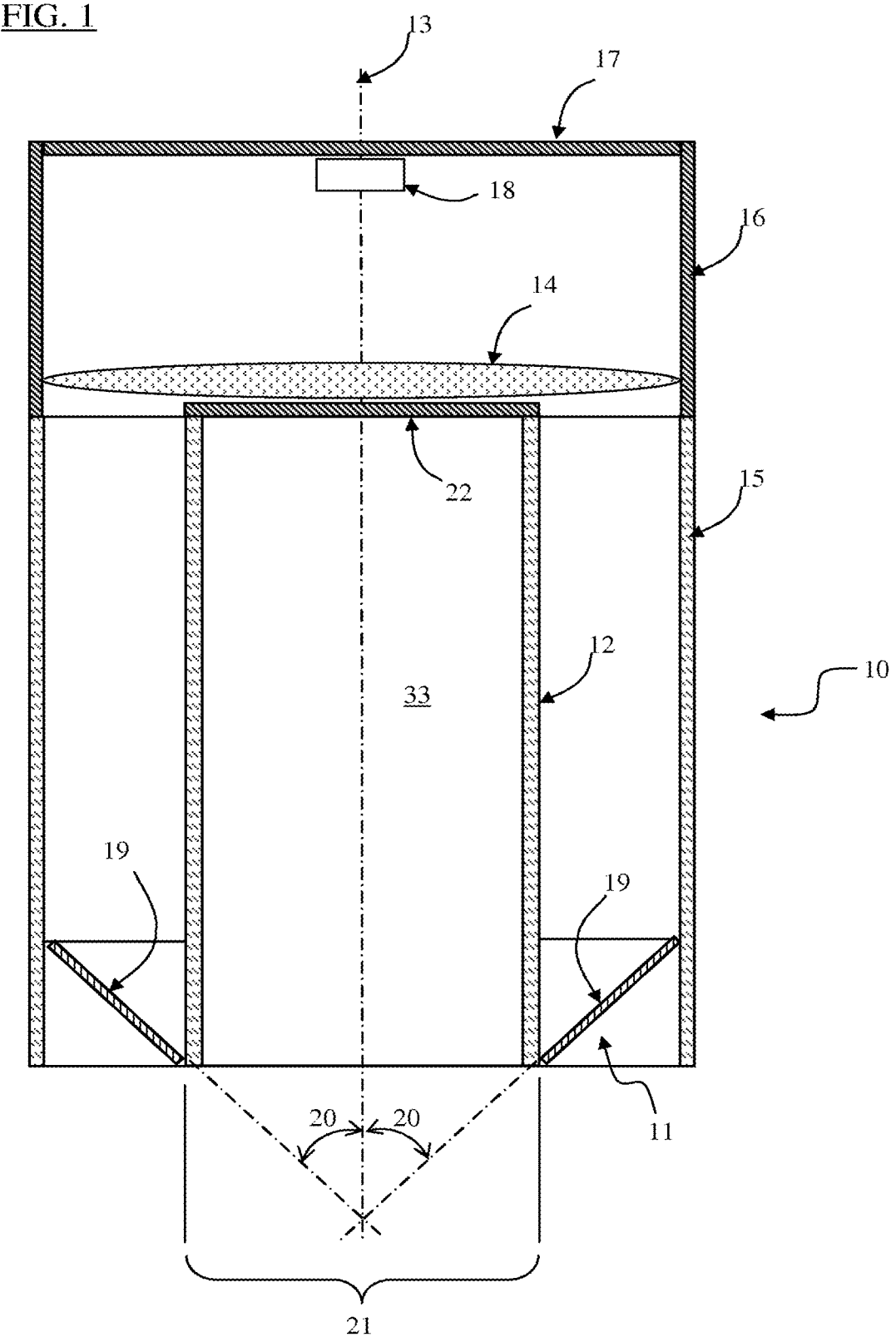
FIG. 1 is a diagram showing an image-taking device in longitudinal section view on a plane containing the axis of symmetry of the reflective optical system of the device.
Figure 2:
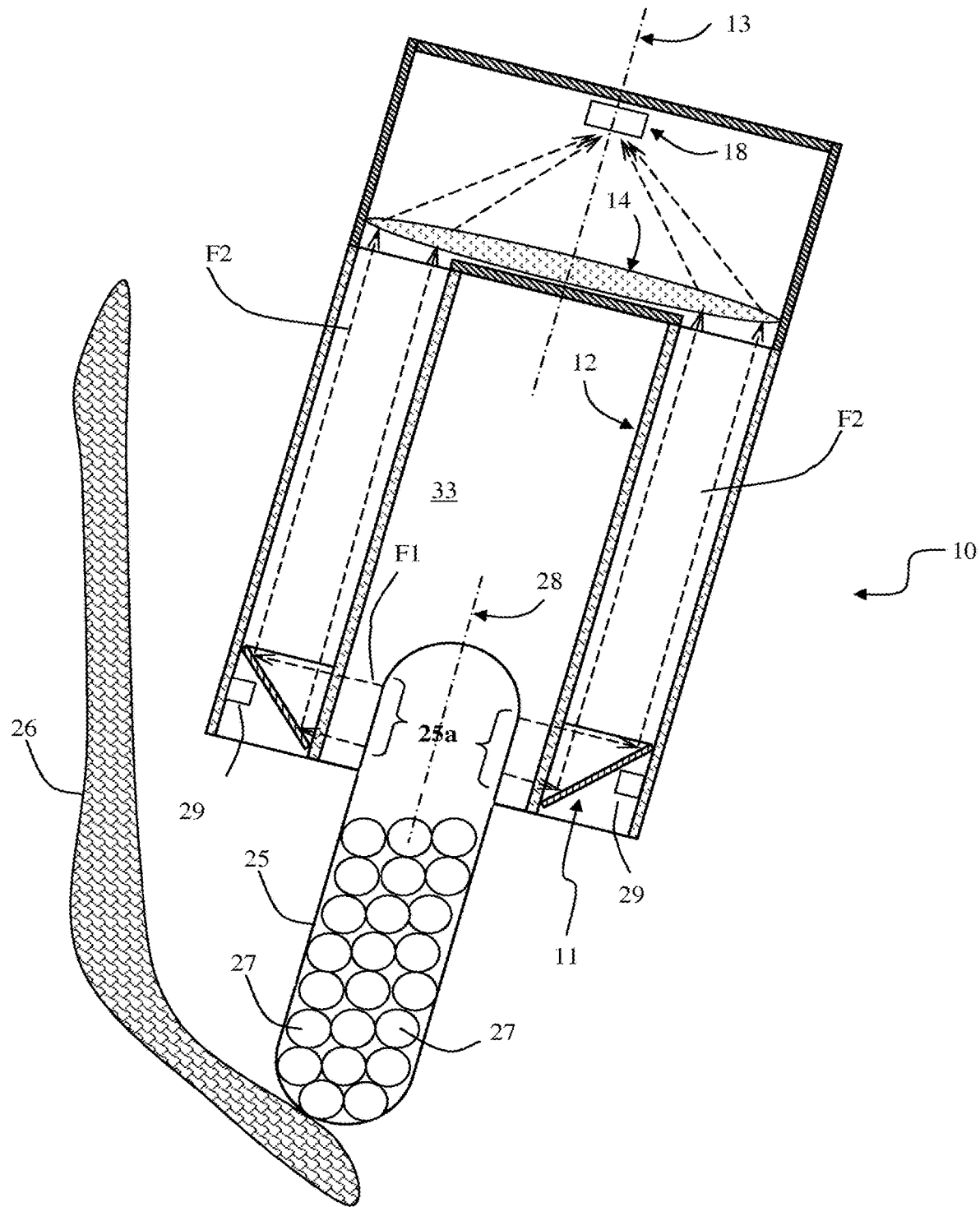
FIG. 2 is a diagram showing the FIG. 1 image-taking device engaged around a terminal portion of a plant such as an ear of maize.
Figure 3:
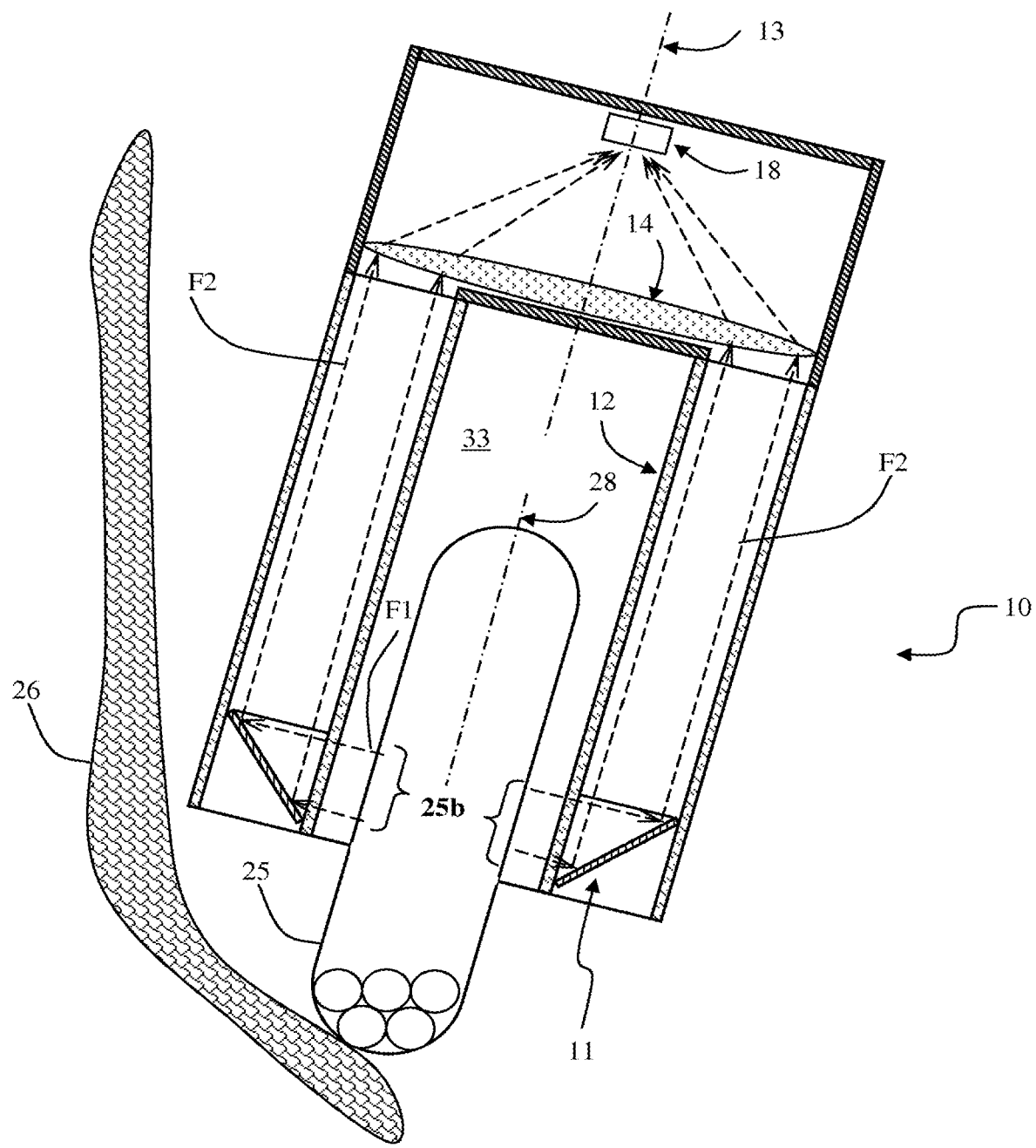
FIG. 3 is a diagram showing the FIG. 1 image-taking device engaged around an intermediate (middle) portion of the plant shown in FIG. 2.

With reference to FIGS. 1 to 3 in particular, the image-taking device 10 has a reflective optical system 11 that is pierced by a central recess 21 and that surrounds an internal window 12.

The optical system 11 is surrounded by an external window 15.

The windows 12 and 15 may be made of a transparent material such as glass. Alternatively, the external window 15 may be opaque.

These windows are generally tubular in shape, in particular they are in the form of cylinders of circular section, about an axis 13 forming the longitudinal axis and general axis of symmetry of the device 10.

The window 12 extends facing the optical system 11 and presents a height (measured along the axis 13) that is not less than the height of the optical system 11.

The optical system 11 comprises at least one mirror 19—or reflecting surface—that is inclined relative to the axis 13 at an acute angle 20, which is substantially equal to 45° in this example, such that the surface 19 faces towards the axis 13 of the device.

Figure 5:
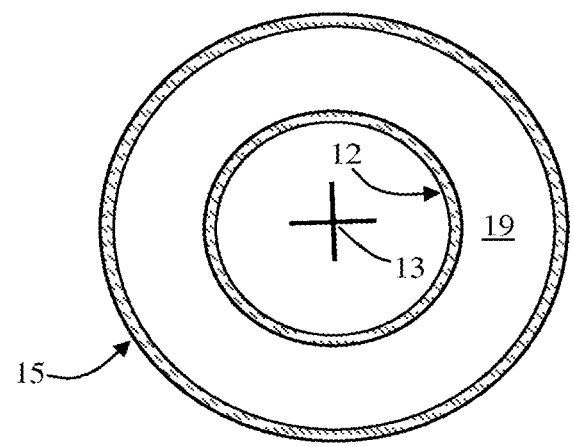
FIG. 5 is a diagram of a reflective optical system and two transparent tubular windows of an image-taking device in cross-section view, perpendicularly to the axis of the reflective optical system and the tubular windows.
Figure 6:
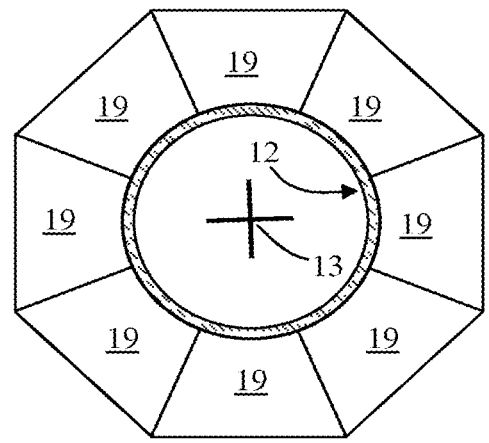
FIG. 6 is a diagrammatic cross-section view showing a reflective optical system surrounding a transparent tubular window of an image-taking device.
Figure 7:
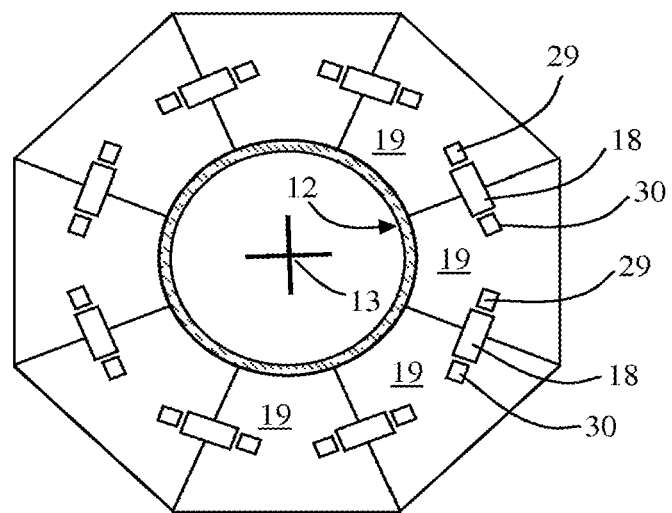
FIG. 7 is likewise a cross-section view showing a reflective optical system surrounding a transparent tubular window, together with the image sensors and the light sources for illuminating and aiming of an image-taking device.

The optical system 11 may comprise a single warped surface 19 of frustoconical shape, as shown in FIG. 5 or a plurality of plane surfaces 19 of curvilinear trapezoidal outline, as shown in FIGS. 6 and 7.

The device 10 also includes an imager comprising an image sensor 18 and an objective lens 14 represented diagrammatically in the form of a lens that is biconvex.

The common optical axis of the sensor 18 and of the lens 14 in this example coincides with the axis 13 of the device 10.

The top end of the internal tubular window 12 in this example is closed by an opaque wall 22 that extends facing the central portion of the lens 14.

The window 12 and the wall 22 thus define a cavity 33 of elongate (cylindrical) shape along the axis 13, with its bottom end surrounded by the window 12 and by the optical system 11, and that is suitable for receiving an article for imaging, as shown in FIGS. 2 and 3.

The device 10 also has an opaque wall 16 extending the window 15 and closed by a wall 17 in order to form a housing that receives the sensor 18 and the lens 14.

Figure 8:
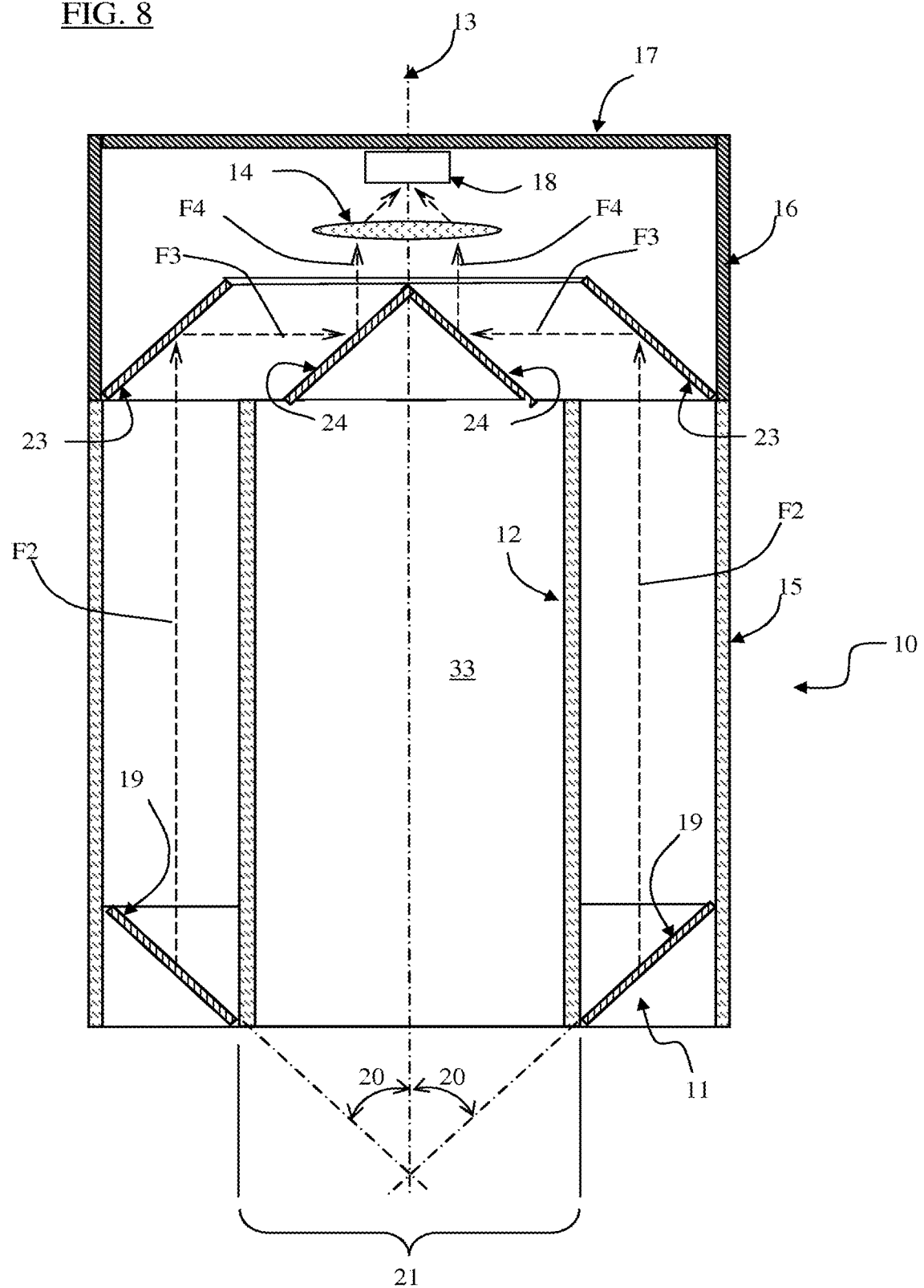
FIG. 8 is a longitudinal section view showing a variant of the FIG. 1 image-taking device, having a device for folding the light beam reflected by the reflective optical system surrounding the article to be imaged.

In the variant embodiment shown in FIG. 8, the device 10 has a beam-folding device arranged on the light path between the imager 14, 18 and the reflecting surface(s) 19 of the optical system 11.

This beam-folding device has a second hollowed-out reflective optical system extending around an axis coinciding with the axis 13 of the first hollowed-out reflective optical system, together with a third reflective optical system on the same axis as the first and second reflective optical systems.

The second reflective optical system has reflective surfaces 23 facing towards the axis 13 that are preferably inclined relative to said axis at an angle of about 45°.

In particular, this second optical system may be substantially symmetrical relative to the first optical system 11 about a transverse midplane (perpendicular to the axis 13).

The second optical system enables a beam F2 coming from the surfaces 19 and propagating parallel to the axis 13 to be reflected so as to produce a beam F3 that propagates radially (relative to the axis 13), towards the axis 13.

The second and third reflective optical systems may comprise respective reflecting surfaces 23, 24 of frustoconical shape about the axis 13.

The reflecting surface(s) 24 of the third optical system, extending facing the surface(s) 23, serve(s) to reflect the beam F3 so as to produce a beam F4 that propagates parallel to the beam F2, closer to the axis 13 and towards the lens 14 which focuses the beam F4 on the sensor 18.

In FIGS. 2 and 3, the device 10 is engaged around a portion of an ear of maize 25 that is still attached to a stem 26 of a maize plant in order to make it possible to determinate characteristic of the ear without removing it from the plant, e.g. in order to count the kernels 27 (shown in part) of the ear on the basis of images of the periphery of the ear that are taken by the device 10.

For this purpose, the device 10 is arranged so as to cover and surround the top portion of the ear 25, which portion penetrates in part into the cavity 33 via the orifice at the bottom end of the tubular window 12.

The device 10 is preferably put into position around the ear 25 so that the top portion—or "slice"—25a of the ear, which extends along the longitudinal axis 28 of the ear, extends substantially along the axis of symmetry 13 of the optical system 11 and of the cavity 33, so that the various portions of the peripheral surface of the portion 25a of the ear are situated at substantially the same distance from the window 12, and consequently from the optical system 11.

With the ear and the image-taking device in this relative position, the light beam F1 reflected by the top peripheral surface 25a of the ear propagates substantially radially relative to the axes 13 and 28, passes through the window 12, and is reflected by the optical system 11 so as to form a beam F2 that propagates substantially parallel to the axis 13.

The beam F2 is focused by the lens 14 on the sensing surface of the sensor 18 so as to form an image of the surface 25a that is captured by the sensor 18 and that can be recorded and processed by a processor unit (such as a microprocessor) that is incorporated in the device 10.

For this purpose, the surface 25a may be illuminated with "natural" (ambient) light passing through the internal and external windows 12 and 15 of the device, and/or by light produced by a light source incorporated in the device 10.

By way of example, this light source may be constituted by light-emitting diodes (LEDs) 29 that are regularly arranged around the optical system 11 (which is then semi-transparent) and that produce light beams that pass through the optical system.

After an image of the top peripheral surface 25a or "slice" has been taken by one or more sensors 18, the device may be moved along the axis 28 of the ear towards the base of the ear in order to take an image of the intermediate peripheral surface 25b of the ear, as in the configuration shown in FIG. 3.

The device 10 is preferably held substantially centered on the article to be imaged, i.e. by keeping the respective axes 13 and 28 of the optical system 11 (and of the cavity 33) and of the article 25 substantially in coincidence.

Figure 4:
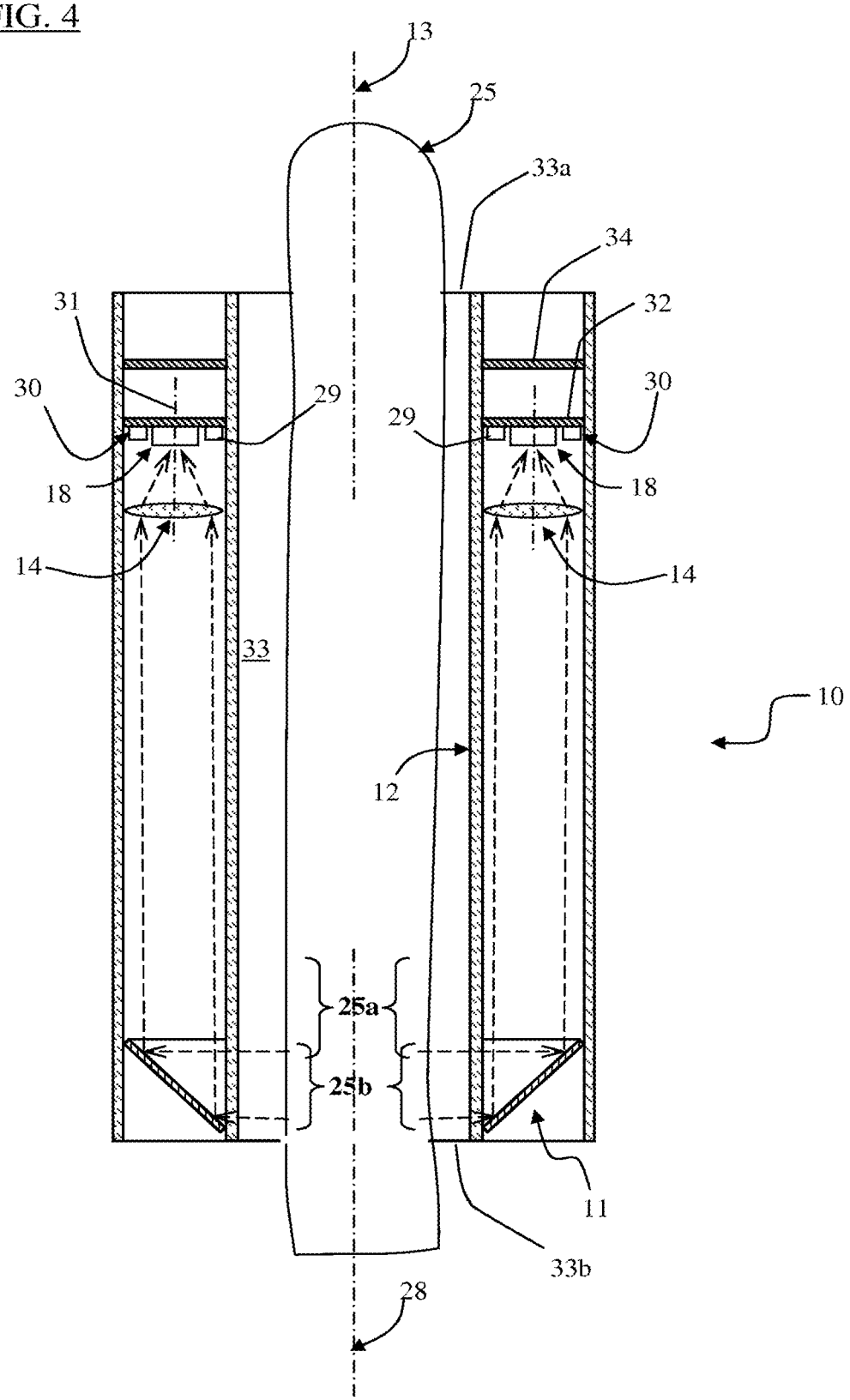
FIG. 4 is a diagram showing another image-taking device in longitudinal section view on a plane containing the axis of symmetry of the reflective optical system of the device, which device is engaged around an article of elongate shape that extends through the image-taking device.

Preferably, the device is moved and successive images of portions 25a, 25b of the article are taken that are spaced apart along the axis 28 in such a manner that the successive images taken overlap in pairs, as shown diagrammatically in FIG. 4, and then these images are processed so as to be connected together by "stacking" their mutual overlap.

The frequency at which these images are acquired can be adapted to the speed at which the device 10 is moved along the article, so as to obtain such overlap between successive images.

For this purpose, the device may have a motion sensor, such as at least one accelerometer or other inertial sensor, which is secured to the first reflective optical system and/or to the body of the device in such a manner as to be sensitive to movement of the device relative to a fixed reference frame—and thus relative to the article 25—, and that is connected to the means for processing the images delivered by the sensor(s) 18 in order to deliver motion signals to which image acquisition can be servo-controlled.

In the embodiment shown in FIG. 4, the device 10 has a plurality of imagers, each having a lens 14 and an image sensor 18. The respective optical axes 31 of the imagers are spaced apart from—and parallel to—the axis 13 of the first reflective optical system, and they are arranged regularly around the axis 13.

The imagers are mounted on an annular (ring shaped) support 32 having a recess centered on the axis 13 and extending in a transverse plane between the internal and external windows 12 and 15.

The imagers deliver signals or data to the image processor means that are mounted on a support 34—such as a printed circuit board—that is likewise ring shaped and that extends between the windows 12 and 15.

The lenses 14 are also fastened to an annular support (not shown) that extends between the windows 12 and 15.

The annular supports 32 and 34 co-operate with the first hollowed-out reflective optical system, and where appropriate with the transparent window, to contribute to defining a cavity 33 that is open at both of its ends 33*a* and 33*b*.

The cavity 33 is suitable for receiving the article that passes right through the device in this example, thereby enabling the device to be moved all along the article for imaging over a distance that is greater than the length of the device (and its cavity).

As shown in FIGS. 4 and 6, a light source 29 is associated with each sensor 18 in order to illuminate a portion for imaging of the periphery of the article, by using the first reflective optical system to reflect a light beam emitted by the light source along a lighting axis that may be parallel to the axis 13.

In the same manner, an aiming light source 30 is associated with each sensor 18 in order to form a light mark on a portion for imaging of the periphery of the article, by using the optical system 11 to reflect a light beam emitted by the aiming source along an aiming axis that may be parallel to the axis 13 of the optical system 11.

As shown in FIG. 7, each sensor 18 has its optical axis crossing a line of separation between two adjacent surfaces 19, and can thus receive an image of a peripheral portion of an article made up of two image portions reflected respectively by the two adjacent surfaces 19.

Furthermore, two adjacent sensors 18 having their respective optical axes respectively crossing two opposite edges of a surface 19 that extends between these axes enable these two sensors to obtain a three-dimensional image of a peripheral portion of an article by stereoscopic vision.

Figure 9:
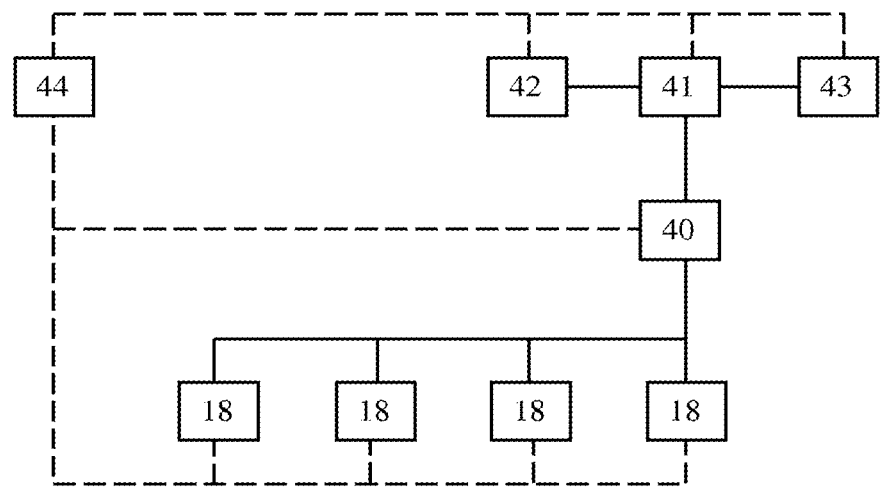
FIG. 9 is a diagram of image processor means connected to a plurality of image sensors of an image-taking device.

With reference to FIG. 9, the device 10 has a first electronic circuit 40 that is connected to four sensors 18 in order to receive the image data captured by the sensors, and suitable for merging the data so as to deliver it to a second electronic circuit 41 that performs image processing, in particular as a function of signals delivered by an accelerometer 43 connected to the circuit 41, and that stores the processed images in a memory 42.

A battery 44 is connected to the sensors 18, 43 and to the circuits 40 to 42 in order to power them.

The device preferably also includes means for identifying an article and/or means for associating at least one kind of identification data with the image (or images) of an article imaged by the device.

The article may be identified "indirectly", e.g. by using geolocation data of an article for the purpose of identifying it.

Under such circumstances, the device may include a receiver for receiving geolocation signals transmitted by satellites, such as a GPS receiver, which receiver is connected to the data processor unit 40, 41; then the geolocation data of the device 10—and consequently of an article surrounded by the device—can be associated by the unit 40, 41—and can be stored together—with the image (or the images) of the article as taken by the device.

Article identification may also consist in associating visual and/or sound information with the image taken of an article.

In order to associate sound information with an image, the device may include a microphone connected to the data processor unit 40, 41, the unit then associating sound data delivered by the microphone with the image (or images) of a determined article, and/or recording the sound data.

In order to associate visual information with an image, the device may include a visual information sensor, e.g. a bar code reader, which sensor is connected to the data processor unit 40, 41, with the data processor unit associating the visual data delivered by the visual information sensor with the image (or images) of a determined article, and/or recording the visual data.

The visual information sensor may be constituted by at least one of the image sensors 18 and the processor unit 40, 41 may then be arranged to extract visual information from the images taken, e.g. in order to extract identification data from the article being imaged, in particular in order to extract identification data (e.g. a bar code) carried by a label placed on the article.

The invention claimed is:

1. A device for taking images of an article, the device comprising:
    a reflective optical system extending around an axis of symmetry, having a recess centered on the axis of symmetry and including at least one reflecting surface facing towards the axis of symmetry, the at least one reflecting surface being inclined relative to the axis of symmetry, at an acute angle of inclination; and
    at least one imager arranged to capture at least one image of at least a portion of the article as reflected by the at least one reflecting surface substantially parallel to the axis of symmetry when the reflective optical system is arranged around the portion of the article; and
    at least one aiming light source arranged to form a light mark on a portion for imaging of a periphery of the article, by using the reflective optical system to form the light mark in a form of a line segment by reflecting a flat light beam emitted by the aiming source along an aiming axis that slopes little, if at all, relative to the axis of symmetry of the reflective optical system.

2. A device for taking images of an article, the device comprising:
    a first reflective optical system extending around an axis of symmetry, having a recess centered on the axis of symmetry and including at least one reflecting surface facing towards the axis of symmetry, the at least one reflecting surface being inclined relative to the axis of symmetry, at an acute angle of inclination;
    at least one light source arranged to (1) emit a light beam along an axis that is inclined little, if at all, relative to the axis of symmetry of the first reflective optical system, (2) reflect the light beam using the at least one reflecting surface, and (3) illuminate, using the light beam reflected using the at least one reflecting surface, a portion for imaging of a periphery of the article; and
    at least one imager arranged to capture at least one image of at least a portion of the article as reflected by the at least one reflecting surface substantially parallel to the axis of symmetry when the first reflective optical system is arranged around the portion of the article.

3. A device according to claim 2, further comprising a transparent window between the axis of symmetry and the first reflective optical system.

4. A device according to claim 3, wherein the transparent window is of cylindrical shape and circular section and interposed between the axis of symmetry and the first reflective optical system.

5. A device according to claim 2, wherein the first reflective optical system is contained within a first cylinder, the recess extending inside a transparent second cylinder surrounded by and coaxial with the first cylinder, and the radius of the first cylinder is less than or equal to three times the radius of the second cylinder.

6. A device according to claim 2, wherein the at least one reflecting surface of the first reflective optical system is a single reflecting surface that is warped, of conical shape, and providing symmetry of revolution about an axis of revolution coinciding with the axis of symmetry.

7. A device according to claim 2, wherein the at least one reflecting surface of the first reflective optical system includes a plurality of reflecting surfaces of identical shape and dimensions, which surfaces are regularly arranged around the axis of symmetry.

8. A device according to claim 2, wherein the at least one reflecting surface is inclined relative to the axis of symmetry at an angle of inclination that is substantially equal to 45 degrees.

9. A device according to claim 2, wherein the at least one reflecting surface is partially reflecting and partially transmissive or transparent.

10. A device according to claim 2, wherein the at least one imager is a single imager with a lens of diameter not less than a largest outside dimension of the first reflective optical system and of optical axis close to and substantially parallel to the axis of symmetry.

11. A device according to claim 10, further comprising a beam-folder device placed on a light path between the single imager and the at least one reflecting surface, the beam-folder device including a second reflective optical system extending around an axis of symmetry coinciding with the axis of symmetry of the first reflective optical system, and a third reflective optical system on a same axis of symmetry as the first and second reflective optical systems.

12. A device according to claim 2, wherein the at least one imager comprises a plurality of imagers with respective optical axes that are spaced apart from, and parallel to, the axis of symmetry of the first reflective optical system, and that are arranged regularly around the axis of symmetry of the first reflective optical system.

13. A device according to claim 12, wherein the plurality of imagers are mounted on at least one annular support providing a recess centered on the axis of symmetry of the first reflective optical system, the at least one annular support co-operating with the first reflective optical system, and with a transparent window, to contribute to defining a cavity configured to receive the article.

14. A device according to claim 2, further comprising at least one signal and/or data processor unit that is connected to the at least one imager and (a) arranged to perform at least some of the image processing required for determining a property of the article from the images acquired by the at least one imager, and/or (b) arranged to extract at least one of visual information from the images taken, data for identifying an article in the images, and identification data carried by a label placed on the article.

15. A device according to claim 14, wherein the at least one signal and/or data processor unit is a data processor unit, the device further comprising a data storage unit connected to the data processor unit and arranged to store image data delivered by the data processor unit.

16. A device according to claim 15, further comprising a battery arranged to power the at least one imager, the data processor unit, and the data storage unit.

17. A device according to claim 2, further comprising means for centering the article in the recess in the first reflective optical system.

18. A device according to claim 2, further comprising members for pressing against the article that are mounted to move relative to the first reflective optical system along radial axes extending in a plane perpendicular to the axis of symmetry of the first reflective optical system.

19. A device according to claim 2, wherein the at least one imager comprises a plurality of image sensors that are arranged regularly around the axis of symmetry of the first reflective optical system,
wherein the plurality of image sensors are mounted on at least one annular support centered on the axis of symmetry of the first reflective optical system, the at least one annular support co-operating with the first reflective optical system and with a transparent window interposed between the axis of symmetry and the first reflective optical system to provide a cavity extending an entire length of a longitudinal direction of the device that is configured to receive the article at one end of the device and pass at least a portion of the article out an opposite end of the device.

20. A method of taking images in situ of an article, the method comprising:
surrounding at least a portion of the article that extends along a longitudinal axis, by at least one reflecting surface directed towards the longitudinal axis, the at least one reflecting surface being inclined relative to the longitudinal axis, at an acute angle of inclination;
emitting from at least one light source a light beam along a first axis that is inclined little, if at all, relative to the axis of symmetry of the at least one reflecting surface;
reflecting the light beam using the at least one reflecting surface;
illuminating, using the light beam reflected using the at least one reflecting surface, a portion for imaging of at least a peripheral portion of the article; and
capturing at least one image of the at least a peripheral portion of the article, which image is reflected by the at least one reflecting surface substantially parallel to the longitudinal axis.

21. A method according to claim 20, wherein image taking is repeated plural times to scan a periphery of the article, and the method further comprising splicing together in pairs the images as taken in succession.

22. A method according to claim 20, wherein the article is a portion of a growing plant.

23. A method according to claim 22, wherein use is made of a device for taking images of the article, the device comprising:
a reflective optical system extending around an axis of symmetry, including a recess centered on the axis of symmetry and including the at least one reflecting surface; and
at least one imager arranged to capture the at least one image when the reflective optical system is arranged around the portion of the article.

24. A method according to claim 23, wherein the device includes a sensor for sensing motion of the device, and a frequency at which images of the article are acquired is matched to a speed the device moves along the article.

25. A method according to claim 23, wherein the device includes two adjacent image sensors with respective optical axes respectively crossing two opposite edges of the at least one reflecting surface that extends between the optical axes, and a three-dimensional image of a peripheral portion of the article is determined by stereoscopic vision.

\* \* \* \* \*